United States Patent [19]

VandenBerg

[11] Patent Number: Plant 7,673

[45] Date of Patent: Oct. 8, 1991

[54] CHRYSANTHEMUM PLANT NAMED DARK YELLOW VERO

[75] Inventor: Cornelis P. VandenBerg, Salinas, Calif.

[73] Assignee: Yoder Brothers, Inc., Barberton, Ohio

[21] Appl. No.: 481,070

[22] Filed: Feb. 16, 1990

[51] Int. Cl.[5] ..... A01H 5/00

[52] U.S. Cl. ..... Plt./74

[58] Field of Search ..... Plt./74

[56] References Cited

U.S. PATENT DOCUMENTS

| | | | |
|---|---|---|---|
| P.P. 5,230 | 5/1984 | Hesse | Plt. 74 |
| P.P. 5,491 | 6/1985 | Shoesmith et al. | Plt. 74 |
| P.P. 6,156 | 4/1988 | Hesse | Plt. 74 |
| P.P. 6,301 | 9/1988 | Van der Knaap | Plt. 74 |
| P.P. 6,399 | 11/1988 | Duffett et al. | Plt. 74 |
| P.P. 6,943 | 7/1989 | Vandenberg | Plt. 74 |
| P.P. 6,954 | 7/1989 | Vandenberg | Plt. 74 |
| 4,616,099 | 10/1986 | Sparkes | 800/1 |

OTHER PUBLICATIONS

Gosling, ed., 1979, "The Chrysanthemum Manual—*6th edition*", The National Chrysanthemum Society, London, Essex Telegraph Press, Ltd., pp. 329–336.

Broertjes et al., 1978, *Application of Mutation Breeding Methods in the Improvement of Vegetatively Propagated Crops*, Elsevier Sci Pub Co., New York, pp. 162–175.

Broertjes et al., 1980, "A mutant of a mutant of a mutant of a . . . Irradiation of progressive radiation-induced mutants in a mutation breeding programme with *Chrysanthemum morifolum*", Euphytica, 29:526–530.

Searle et al., 1968, "*Chrysanthemum the Year Round*", Blanford Press, London, pp. 27–29, 320–327.

Chan, 1966, "Chrysanthemum and nose mutations induced by X-rays", Am. Soc. Hort. Sci. Proc., pp. 613–620.

Broertjes, 1966, "Mutation breeding of chrysanthemums", Euphytica, 15:156–162.

Dowrick et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Dark Yellow Vero particularly characterized by its flat capitulum form; daisy capitulum type; yellow ray floret color with good color retention; diameter across face of capitulum of 85 to 89 mm when fully opened; photoperiodic flowering response to short days of 56 to 63 days when grown in Salinas; plant height when grown as a single stem spray cut mum in Salinas with 14 long days prior to start of short days in 89 to 119 cm; and excellent tolerance to low temperatures for bud initiation and flower development.

1 Drawing Sheet

The present invention comprises a new and distinct cultivar of Chrysanthemum, botanically known as *Dendranthema grandiflora*, and referred to by the cultivar name Dark Yellow Vero.

Dark Yellow Vero, identified as 81-064H02, is a product of a mutation inducation program. The new cultivar was discovered and selected by Cornelis P. VandenBerg on Dec. 21, 1987 in a controlled environment in Salinas, Calif. as one flowering plant within a flowering block established as rooted cuttings from stock plants which had been exposed as unrooted cuttings to an X-ray source of 1,750 rads. The irradiated parent cultivar was an unnamed mutation identified as 81-064G02, which was selected as a pale yellow color sport from a mutation induction program of the parent cultivar Vero, a white daisy spray cut mum disclosed in U.S. Plant Pat. No. 6,399.

The first act of asexual reproduction of Dark Yellow Vero was accomplished when vegetative cuttings were taken from the initial selection in February 1988 in a controlled environment in Salinas, Calif., by technicians working under the supervision of Cornelis P. VandenBerg.

Horticultural examination of controlled flowerings of successive plantings has shown that the unique combination of characteristics as herein disclosed for Dark Yellow Vero are firmly fixed and are retained through successive generations of asexual reproduction.

Dark Yellow Vero has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

The following observations, measurements and comparisons describe plants grown in Salinas, Calif. and in Bogota, Colombia under greenhouse conditions which approximate those generally used in commercial greenhouse practice. The low temperature tolerance was determined by repeated flowerings in Bogota, Colombia.

The following traits have been repeatedly observed and are determined to be basic characteristics of Dark Yellow Vero, which, in combination, distinguish this Chrysanthemum as a new and distinct cultivar:

1. Flat capitulum form.
2. Daisy capitulum type.

3. Yellow ray floret color.

4. Diameter across face of capitulum of 85 to 89 mm when fully opened.

5. Flowering response in Salinas under normal temperatures is 56 to 63 days after start of short days.

6. Plant height is 89 to 119 cm when grown in Salinas as a single stem cut spray mum with 14 long days after planting prior to start of short days.

7. Excellent tolerance to low temperatures for bud initiation and flower development. Average minimum low night temperatures in our Bogota trials ranged from 7 to 8.5 degrees Celsius.

The accompanying photographic drawing shows typical inflorescence and leaf characteristics of Dark Yellow Vero, with the colors being as nearly true as possible with illustrations of this type. The color photograph is a perspective view of Dark Yellow Vero grown as a single stem cut spray mum.

Of the commercial cultivars known to the inventor, the most similar in comparison to Dark Yellow Vero is the cultivar Yellow Vero, disclosed in U.S. Plant Pat. No. 6,943. All traits of Dark Yellow Vero are similar to those of Yellow Vero, except ray floret color and color retention. The color of the ray florets of Dark Yellow Vero is a darker, more intense yellow than the ray floret color of Yellow Vero, which is 4B when the flower is fully open. The color 4B is a relatively light, soft yellow which sharply contrasts to the intense bright yellow of the new cultivar. Moreover, Yellow Vero has a tendency to fade rapidly to an even lighter yellow, as contrasted with Dark Yellow Vero which has a significantly better color retention.

Dark Yellow Vero can also be compared to Vero and Cream Vero (U.S. Plant Pat. No. 6,954). Dark Yellow Vero is distinguished both from its grandparent cultivar Vero and the cultivar Cream Vero (induced mutation of Vero) only by its ray floret color. The ray floret color of Vero is white, and the ray floret color of Cream Vero is light yellow (RHS 5D).

In the following description color references are made to The Royal Horticultural Society Colour Chart. The color values were determined on plant material grown as a single stem cut spray mum in Salinas, Calif. on July 24, 1989.

Classification:

*Botanical.*—*Dendranthema grandiflora* cv Dark Yellow Vero.

*Commercial.*—Daisy cut spray mum.

INFLORESCENCE

A. Capitulum:

*Form.*—Flat.

*Type.*—Daisy.

*Diameter across face.*—85 to 89 mm when fully opened.

B. Corolla of ray florets:

*Color (general tonality from a distance of three meters).*—Yellow.

*Color (upper surface).*—6A, oxidizing to 6B and 6C.

*Color (under surface).*—6C to 6D.

*Shape.*—Flat, oblong.

C. Corolla of disc florets:

*Color (mature).*—Closest to 12A to 12B.

*Color (immature).*—Closest to 144A to 144B.

D. Reproductive organs:

*Androecium.*—Present on disc florets only: scant pollen.

*Gynoecium.*—Present on both ray and disc florets.

PLANT

A. General appearance:

*Height.*—89 to 119 cm when grown in Salinas as a single stem cut spray mum with 14 long days after planting prior to start of short days.

B. Foliage:

*Color (upper surface).*—137A.

*Color (under surface).*—137B.

*Shape.*—Lobed, slightly serrated.

*Size.*—Normal.

I claim:

1. A new and distinct Chrysanthemum plant named Dark Yellow Vero, as described and illustrated.

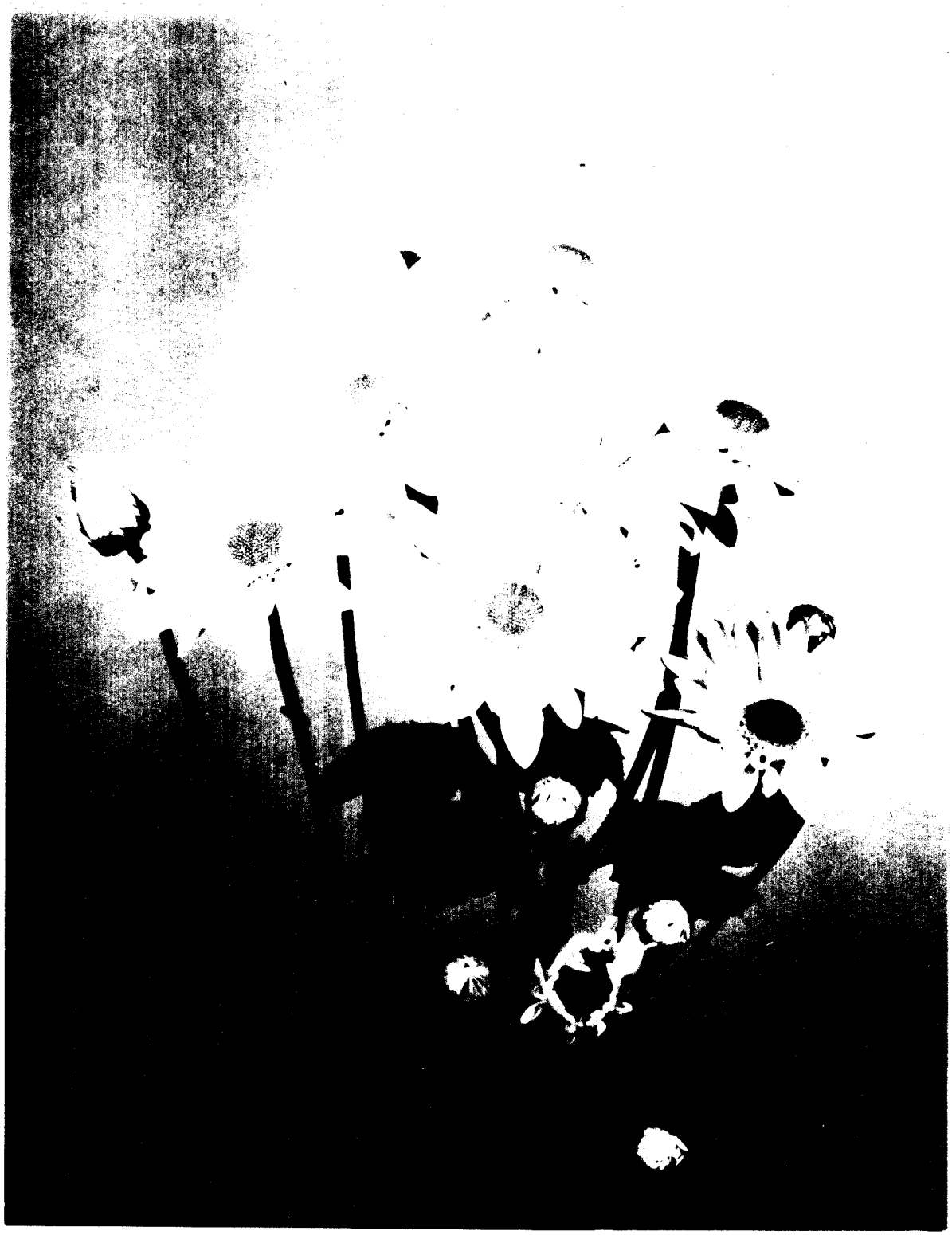

* * * * *